United States Patent [19]

Collins et al.

[11] Patent Number: 4,604,400

[45] Date of Patent: Aug. 5, 1986

[54] TREATING ARTHRITIS WITH 3-(N,N-DIMETHYL CARBAMOYL)PYRAZOLO[1,5-A]PYRIDINE

[75] Inventors: Raymond F. Collins, Harold Wood; Christopher A. Ramsden, Brentwood; Libert C. Saunders, Grays; Peter J. Warne, London, all of England

[73] Assignee: May & Baker Limited, Essex, England

[21] Appl. No.: 649,980

[22] Filed: Sep. 13, 1984

Related U.S. Application Data

[63] Continuation of Ser. No. 504,438, Jun. 15, 1983, abandoned.

[30] Foreign Application Priority Data

Jun. 16, 1982 [GB] United Kingdom ................ 8217485

[51] Int. Cl.$^4$ .............................................. A61K 31/44
[52] U.S. Cl. .................................... 514/300; 546/121
[58] Field of Search ......................... 546/121; 514/300

[56] References Cited

FOREIGN PATENT DOCUMENTS 56-10114 2/1981 Japan .
56-51478 5/1981 Japan .
1528807 10/1978 United Kingdom .

OTHER PUBLICATIONS

Chemical Abstracts vol. 95, P115542g (1981).
Chemical Abstracts vol. 94, P180683x (1981).

*Primary Examiner*—Henry R. Jiles
*Assistant Examiner*—Bernard I. Dentz
*Attorney, Agent, or Firm*—Stevens, Davis, Miller & Mosher

[57] ABSTRACT

3-(N,N-Dimethylcarbamoyl)pyrazolo[1,5-a]pyridine of the formula:

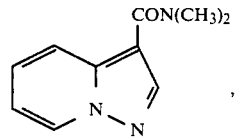

which is a new compound, possesses pharmacological properties, in particular properties which are indicative of outstanding utility in the treatment of arthritic disorders such as rheumatoid arthritis. The compound can be prepared by reacting a pyrazolo[1,5-a]pyridine-3-carbonyl halide (e.g. chloride) with dimethylamine.

2 Claims, No Drawings

TREATING ARTHRITIS WITH 3-(N,N-DIMETHYL CARBAMOYL)PYRAZOLO[1,5-A]PYRIDINE

This application is a continuation of application Ser. No. 504,438, filed 6/15/83, now abandoned.

DESCRIPTION

This invention relates to a new therapeutically useful pyrazolopyridine derivative, to a process for its preparation, to pharmaceutical compositions containing it, and to its use as a pharmaceutical.

The new pyrazolopyridine derivative is 3-(N,N-dimethylcarbamoyl)pyrazolo[1,5-a]pyridine of the formula:

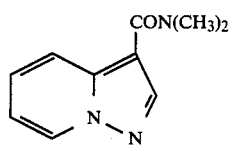

The compound has valuable pharmacological properties, in particular properties which are indicative of outstanding utility in the treatment of arthritic disorders such as rheumatoid arthritis. In particular, in laboratory tests, the compound has been shown to inhibit the deterioration of joints in rabbits' limbs. These results are particularly important because compounds currently employed in the treatment of arthritic disorders are primarily antiinflammatories and do not possess the said ability to inhibit joint deterioration. Furthermore, the compound of formula I surprisingly is markedly superior in its antiarthritic properties even when compared with very closely related compounds.

The beneficial properties of the compound of formula I are enhanced by the fact that it has only very low mammalian toxicity.

Furthermore, the fact that it is soluble in water renders it particularly convenient to administer to the patient in pharmaceutical compositions as described hereinafter.

In tests, the compound of formula I when twice administered orally to mice, each time at the dose shown in the following Table I, reduced by 50% the inhibition of migration of incubated mouse macrophage cells. This is a measure of antagonism or reduction of the levels of lymphokines and is indicative of utility in the treatment of arthritic patients.

TABLE I

| Test No. | Oral Dose mg/kg animal body weight |
| --- | --- |
| 1 | 5.0 |
| 2 | 2.5 |
| 3 | 3.5 |
| 4 | 4.0 |
| 5 | 3.5 |

In acute oral toxicity tests mice were dosed orally with the compound of formula I and observed for 3 days. The resulting LD50 figure was 584 mg/kg animal body weight.

The compound of formula I may be prepared by the application or adaptation of known methods.

Thus, as a feature of the present invention, the compound of formula I is prepared by the reaction of an acid halide of the general formula:

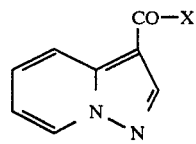

(wherein X represents a halogen, e.g. chlorine, atom) with dimethylamine. Generally the reaction takes place in an organic solvent medium, e.g. a mixture of ethanol and dichloromethane, at temperatures between 0° C. to room temperature, and in the presence of an excess of the dimethylamine.

Compounds of formula II may be prepared from the corresponding acid of the formula:

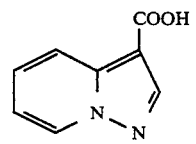

by the application or adaptation of known methods, for example conversion to an alkali metal salt, e.g. the potassium salt, by reaction with a solution of an alkali metal hydroxide, e.g. potassium hydroxide, in a suitable solvent, e.g. methanol, followed by reaction of the resulting salt with the appropriate oxalyl halide, e.g. oxalyl chloride when X represents a chlorine atom in formula II.

The compound of formula III is a known compound and may be prepared by the application of known methods.

By the term "known methods" as used in this specification is meant methods heretofore used or described in the literature.

The following Example illustrates the preparation of the compound of formula I, and the Reference Example illustrates the preparation of the intermediates of formula II.

EXAMPLE 1

A solution of dimethylamine in ethanol (35% w/v; 300 ml) was added to dichloromethane (1100 ml) and the resulting solution was stirred at 0° C. and treated slowly with a solution of pyrazolo[1,5-a]pyridine-3-carbonyl chloride (61.0 g) in dry dichloromethane (1100 ml). When the addition was complete, the mixture was allowed to warm up to room temperature and stand at room temperature overnight. The mixture was then washed twice with water and the organic solution was then dried over sodium sulphate and evaporated under reduced pressure. The resulting brown oil was recrystallised from cyclohexane, to give 3-(N,N-dimethylcarbamoyl)pyrazolo[1,5-a]pyridine (42.0 g), m.p. 86°-87° C.

REFERENCE EXAMPLE I

Pyrazolo[1,5-a]pyridine-3-carboxylic acid (9.72 g) was dissolved in hot anhydrous methanol (225 ml) and treated with a solution of potassium hydroxide (3.73 g) in dry methanol (45 ml) with stirring. The resulting orange solution was evaporated to dryness under reduced pressure, to give a colourless solid. This solid was treated with dry toluene (300 ml) and the mixture was stirred and treated with oxalyl chloride (10.2 ml), with stirring, at room temperature. After further stirring for a period of 15 minutes the mixture was treated with pyridine (45 drops), and the mixture was vigorously stirred overnight. The mixture was then filtered and the filtrate was evaporated under reduced pressure, to give pyrazolo[1,5-a]pyridine-3-carbonyl chloride (10.6 g), m.p. 119°–120° C. (in a sealed tube).

The present invention includes within its scope pharmaceutical compositions which comprise the compound of formula I in association with a pharmaceutically acceptable carrier or coating. In clinical practice the compositions of the present invention will normally be administered orally or rectally, or parenterally, for example topically or intraarticularly.

Aqueous solutions, and compositions containing them, are particularly convenient means of administering the compound of formula I.

Solid compositions for oral administration include compressed tablets, pills, dispersible powders, and granules. In such solid compositions the active compound is mixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically acceptable emulsions, solutions, suspensions, and elixirs containing inert diluents commonly used in the art, such as water and liquid paraffin. Besides inert diluents such compositions may also comprise adjuvants, such as wetting and suspending agents, and sweetening, flavouring, perfuming and preserving agents.

The compositions according to the invention, for oral administration, also include capsules of absorbable material such as gelatin containing the active compound with or without the addition of diluents or excipients.

Solid compositions for rectal administration include suppositories formulated in manner known per se and containing the active compound.

Preparations according to the invention for parenteral administration include sterile aqueous or non-aqueous solutions, suspensions, or emulsions. Examples of non-aqueous solvents or suspending media are propylene glycol, vegetable oils such as olive oil, and injectable organic esters such as ethyl oleate. These compositions may also contain adjuvants such as preserving, wetting, emulsifying and dispersing agents. They may be sterilised, for example, by filtration through a bacteria-retaining filter, by incorporation of sterilising agents in the compositions, by irradiation, or by heating. They may also be manufactured in the form of sterile solid compositions, which can be dissolved in a sterile injectable medium immediately before use. As well as the more customary intravenous and intramuscular routes, the compositions may be administered by intraarticular injection.

Compositions in the form of solutions or suspensions, if desired together with additives as described above, in water or in vegetable or other greases, paraffin or other waxes, or lacquers or creams or lotions, to be applied topically, for example to the skin area around an affected joint to relieve arthritis, are also included in the invention. They may also include additives such as nicotinamide to assist absorption.

The percentages of active ingredient in the compositions of the invention may be varied, it being necessary that they should constitute a proportion such that a suitable dosage for the desired antiarthritic effect shall be obtained. Obviously several unit dosage forms may be administered at about the same time. Generally the compositions should contain 0.1% to 80% by weight of active ingredient, especially when in tablet form.

The dose employed depends upon the desired antiarthritic effect, the route of administration and the duration of the treatment. In the adult, the doses are generally between 0.01 and 100 mg (preferably between 0.1 and 10 mg) of the compound of formula I per kg body weight per day.

The compound of formula I may be administered each day or, according to the wishes of the medical practitioner, less often, e.g. weekly.

The present invention provides a method of treating arthritic disorders in man which comprises administering to the patient an amount of the compound of formula I sufficient to combat an arthritic disorder.

The following Composition Examples illustrate pharmaceutical compositions according to the present invention.

Composition Example 1

Capsules for oral administration were made up in the usual manner by filling No. 2 size gelatin capsules each with 155 mg of the following composition:

| | |
|---|---|
| 3-(N,N—dimethylcarbamoyl)pyrazolo[1,5-a]pyridine | 50 mg |
| potato starch | 100 mg |
| magnesium stearate | 2.5 mg |
| Aerosil | 2.5 mg |

Composition Example 2

An aqueous solution was prepared in the usual manner from 3-(N,N-dimethylcarbamoyl)pyrazolo[1,5-a]pyridine (10 g) and water (100 ml).

We claim:

1. A method for the treatment of a patient with an arthritic disorder which comprises administering to the patient an amount of 3-(N,N-dimethylcarbamoyl)pyrazolo[1,5-a]pyridine sufficient to ameliorate the condition of the patient.

2. A method according to claim 1 in which the amount of 3-(N,N-dimethylcarbamoyl)pyrazolo[1,5-a]pyridine administered to an adult patient is between 0.01 and 100 mg per kg body weight per day.

* * * * *